US00PP15222P3

(12) United States Plant Patent
Gray

(10) Patent No.: US PP15,222 P2
(45) Date of Patent: Oct. 12, 2004

(54) ***HYDRANGEA* HYBRID PLANT NAMED 'SWEET CHRIS'**

(50) Latin Name: *Hydrangea macrophylla×serrata×Hydrangea serrata×macrophylla*
Varietal Denomination: Sweet Chris

(75) Inventor: Joseph Gray, Winters, CA (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/357,938

(22) Filed: Feb. 3, 2003

(65) Prior Publication Data

US 2004/0154063 P1 Aug. 5, 2004

(51) Int. Cl.[7] ..... A01H 5/00
(52) U.S. Cl. ..... Plt./250
(58) Field of Search ..... Plt./250

*Primary Examiner*—Kent Bell
(74) *Attorney, Agent, or Firm*—Christie, Parker & Hale, LLP

(57) ABSTRACT

A new plant variety of *Hydrangea* hybrid characterized by dark green foliage, burgundy fall foliage, lacecap flower color and burgundy stem color.

1 Drawing Sheet

Figure 1:
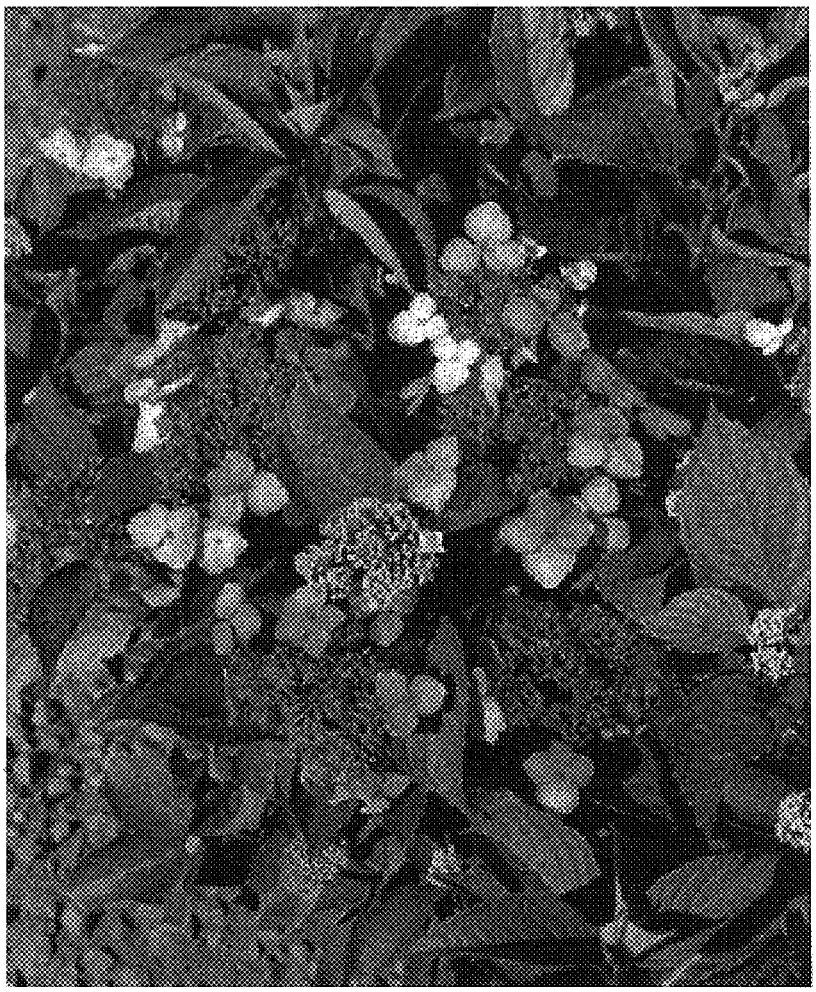

Classification: *Hydrangea* (Thunb.) (*macrophylla×serrata*)×*Hydrangea* (*serrata×macrophylla*).

Varietal denomination: The new plant has the varietal denomination 'Sweet Chris'.

BACKGROUND OF THE INVENTION

The present invention relates to a new and distinct variety of *Hydrangea* hybrid which was developed in a controlled breeding program in Silver Spring, Md., United States, by Mr. Joseph Gray. The varietal denomination of the new variety is 'Sweet Chris'.

The genus *Hydrangea* is included in the family Saxifragaceae which comprises about 80 genera and 1,200 species of herbs, shrubs, small trees and woody climbers mostly temperate in origin. *Hydrangea* comprises approximately 23 species of deciduous or evergreen shrubs and vines originating in North America, South America and East Asia, many of which possess desirable ornamental characteristics. Recent taxonomical treatments sometimes isolate *Hydrangea* in a new family, Hydrangeaceae.

*Hydrangea macrophylla* is widespread and common throughout much of Japan. It generally has opposite, simple leaves, obovate to elliptic in shape, 10 to 20 cm long and 5 to 15 cm wide. Leaf color ranges from light to dark green, depending on light intensity and cultural conditions. Leaves are generally softly pubescent. Flower color is dependent upon the pH level of the soil and the amount of available aluminum in the soil media. Flowers of *Hydrangea macrophylla* are borne in mostly sterile florets, formed in what is often called a "hortensia" flower.

*Hydrangea serrata* is widespread and common throughout much of Japan, Korea and China. It generally has opposite, simple leaves, lanceolate in shape with acuminate apices, 5 to 15 cm long and 5 to 10 cm wide. Leaf color ranges from light to dark green, depending on light intensity and cultural conditions. Leaves are generally softly pubescent. The plant is deciduous. Flower color is dependent upon the pH level of the soil and the amount of available aluminum in the soil media. Flowers of *Hydrangea serrata* are borne in mostly flattened corymbs, 1 to 5 cm wide, with up to 12 sterile florets.

SUMMARY OF THE INVENTION

The new variety was developed in a controlled breeding program of *Hydrangea macrophylla* and *Hydrangea serrata,* and differs from its parents in its dark green summer foliage, burgundy fall foliage, lace cap flower color, and burgundy stem color. Asexual reproduction of the new variety by stem cuttings, performed in Silver Springs, Md. and Vacaville, Calif., have confirmed that the distinctive characteristics of the new variety are stable and transmitted to succeeding generations, and the new variety reproduces true to type.

COMPARISON WITH PARENTS

'Sweet Chris' is distinguished from its parents and all other varieties of *Hydrangea* of which I am aware by dark green summer foliage, burgundy fall foliage, lacecap flower color, and burgundy stem color.

BRIEF DESCRIPTION OF ILLUSTRATION

The accompanying illustration shows a specimen of the new cultivar in a photo illustration as true to color as is reasonably possible to make in an illustration of this character.

FIG. 1 illustrates the inflorescence and overall habit of 'Sweet Chris'.

DETAILED DESCRIPTION OF THE NEW VARIETY

'Sweet Chris' has not been observed under all possible environmental, cultural and light conditions. The following observations and descriptions are of plants grown in Vacaville, Calif. In this description, color references are to The Royal Horticultural Society Colour Chart (1995) and terminology used in the color descriptions herein refers to plate numbers in this color chart. Phenotypic expression may vary with light intensity, cultural and environmental conditions.

CLASSIFICATION

Botanical: *Hydrangea* (Thunb.) *Hydrangea* (Thunb.) (*macrophylla*×*serrata*)×*Hydrangea* (*serrata*×*macrophylla*) 'Sweet Chris'.

Parentage:

*Mother plant.*—*Hydrangea* (*macrophylla*×*serrata*) 'Lanarth White' (unpatented).

*Father plant.*—*Hydrangea* (*serrata*×*macrophylla*) 'Preziosa' (unpatented).

Propagation: By vegetative cuttings.

The following plant descriptors and color readings are of typical 3-year old specimens in 5-gallon nursery containers grown in Vacaville, Calif. under 50% shade, in a 6.6 pH soiless nursery growing media.

PLANT

Size: Approximately 1 m tall and 90 cm wide.

Habit: Upright, compact shrub.

Branching:

*Lateral branches.*—Approximately 30.

*Typical # branches.*—About 30.

*Size.*—Usually up to about 90 cm long.

*Diameter.*—About 7 mm.

*Lenticles.*—Near Red-Purple Group 59C.

*Branch color.*—June–September: Near Red Purple Group 59C. April–May; October–November: Near Green Group 138C.

LEAF

Shape: Ovate to broadly ovate, with a cuneate base and acute to acuminate apex.

Size: Usually up to about 130 mm long and 80 mm wide.

Arrangement: Opposite.

Margin: Serrate.

Texture/substance: Firm to coriaceous glabrous to nearly dull above, glabrous beneath, veins depressed above and raised beneath.

Color:

*Young foliage.*—Top and Bottom near Yellow-Green Group 149A.

*Mature foliage.*—Upper side: Near Yellow-Green Group 146B. Under side: Near Yellow-Green Group 144B.

Venation:

*Pattern.*—Alternately pinnate, sunken above, raised beneath.

*Coloration.*—New Foliage: Upper Surface: Near Green Group 138B. Under Surface: Near Green Group 138B. Mature Foliage: Upper Surface: Near Green Group 139A. Under Surface: Near Green Group 139A.

Fall foliage: Upper Surface: Near Greyed-Purple Group 187A.

Petioles:

*Size.*—About 2.5 to 3 cm long.

*Coloration.*—Upper Surface: Near Red Group 59C. Under Surface: Near Green Group 138D.

*Texture.*—Smooth.

Internodes: About 25 mm.

Hardiness: USDA Zone 6 (−10° F. to 0° F.).

Vigor: Vigorous growth.

Pests/diseases: Resistance to known *Hydrangea* pests and/or diseases has not been observed on plants grown under conditions approximating commercial practices.

Soil pH: 6.6 pH in a soiless nursery growing media.

INFLORESENCE

Bloom period:

*Outdoors.*—April to September.

Flower form: Paniculate, compound corymb inflorescence; both sterile (about 65), sepalous florets and fertile (about 10), asepalous florets borne on same panicle.

Flower arrangement: Loose tiered corymb about 15 to 18 cm across.

Size of inflorescence: About 18 cm.

Shape of inflorescence: Hemispherical.

Fragrance: None.

Lastingness of individual blooms: Flowers are very persistent, lasting up to 5 months. As the flowers mature, the pedicels bearing the outer florets bend to invert the florets toward the ground.

Sepalous florets:

*Sepals.*—Number: Usually 4 sepals per floret, occasionally 3. Shape: Broadly ovate. Apex: Acute. Base: Cuneate. Size: Variable; typical sepal measures about 20 mm by 25 mm. Margin: Dentate to crenate on the upper half of sepal. Curvature: Reflexed. Arrangement: Overlapping at base to midpoint. Color Upper Side: Bicolored; centers near Red-Purple Group 58B in early bloom, maturing to near Red-Purple Group 63A and eventually 61B; margins near Violet Group 83B. Lower Side: Bicolored; centers near Red-Purple Group 58C in early bloom, maturing to near Red-Purple Group 63A and eventually 61B; margins near Violet Group 83B. Size of one large 4-petaled floret: About 3 cm wide. Aspect of sepals: Smooth. Depth of Typical Sepalous Floret: Less than about 1 mm.

Pedicels:

*Length.*—About 2 to 3 cm.

*Diameter.*—Less than about 1 mm.

*Color.*—Near Greyed-Orange Group 177D.

Peduncles:

*Length.*—About 1.8 to 2.2 cm.

*Diameter.*—Approximately 2 mm.

*Color.*—Near Greyed-Orange Group 177D.

Non-sepalous florets:

*Size of floret.*—Approximately 2 mm in diameter.

*Depth of typical non-sepalous floret.*—Less than about 1 mm.

*Color of floret.*—Near Red-Purple Group 63B.

Pedicels:

*Length.*—About 5 to 7 mm.

*Diameter.*—Less than about 1 mm.

*Color.*—Near Greyed-Orange Group 177D.

Peduncles:

*Length.*—About 1.8 to 2.2 cm.

*Diameter.*—Approximately 2 mm.

*Color.*—Near Greyed-Orange Group 177D.

REPRODUCTIVE ORGANS

Stamens: Approximately 8.

Stigma: Usually 4, occasionally 3 or 5.

Pollen amount: Very little, not measurable.

Pollen color: Near White Group 155D.

Fertile inflorescence:

*Pistil length.*—About 2 mm.

*Stigma color.*—Near Red-Purple Group 57D.

*Style color.*—Near Red-Purple Group 57D.

*Ovary color.*—Near Red-Purple Group 57D.

*Stamen filament.*—Near Red-Purple Group 57C.

*Fruit.*—None noted.

I claim:

1. A new and distinct variety of *Hydrangea* plant substantially as shown and described.

* * * * *